US010707490B2

(12) United States Patent
Sugiyama et al.

(10) Patent No.: US 10,707,490 B2
(45) Date of Patent: Jul. 7, 2020

(54) POLYMER COMPOUND, INTERMEDIATE COMPOSITION, NEGATIVE ELECTRODE, ELECTRICITY STORAGE DEVICE, SLURRY FOR NEGATIVE ELECTRODES, METHOD FOR PRODUCING POLYMER COMPOUND, AND METHOD FOR PRODUCING NEGATIVE ELECTRODE

(71) Applicant: KABUSHIKI KAISHA TOYOTA JIDOSHOKKI, Aichi-ken (JP)

(72) Inventors: Yusuke Sugiyama, Kariya (JP); Takeshi Kondo, Kariya (JP); Nobuhiro Goda, Kariya (JP); Masakazu Murase, Kariya (JP)

(73) Assignee: KABUSHIKI KAISHA TOYOTA JIDOSHOKKI, Toyota-shi, Aichi-ken (JP)

( * ) Notice: Subject to any disclaimer, the term of this patent is extended or adjusted under 35 U.S.C. 154(b) by 247 days.

(21) Appl. No.: 15/528,776

(22) PCT Filed: Oct. 30, 2015

(86) PCT No.: PCT/JP2015/080632
§ 371 (c)(1),
(2) Date: May 23, 2017

(87) PCT Pub. No.: WO2016/084548
PCT Pub. Date: Jun. 2, 2016

(65) Prior Publication Data
US 2017/0331114 A1 Nov. 16, 2017

(30) Foreign Application Priority Data
Nov. 25, 2014 (JP) .................. 2014-238097

(51) Int. Cl.
*H01M 4/62* (2006.01)
*C08F 8/40* (2006.01)
*H01G 11/06* (2013.01)
*H01G 11/38* (2013.01)
*C08F 8/42* (2006.01)
*H01M 4/134* (2010.01)
*H01M 4/133* (2010.01)
*C08F 8/32* (2006.01)
*H01M 4/1393* (2010.01)
*H01M 4/587* (2010.01)
*H01M 4/1395* (2010.01)
*H01M 4/04* (2006.01)
*H01M 4/38* (2006.01)
*C07C 211/55* (2006.01)
*C08F 20/02* (2006.01)
*H01M 10/052* (2010.01)
*H01M 10/05* (2010.01)

(52) U.S. Cl.
CPC ........... *H01M 4/622* (2013.01); *C07C 211/55* (2013.01); *C08F 8/32* (2013.01); *C08F 8/40* (2013.01); *C08F 8/42* (2013.01); *C08F 20/02* (2013.01); *H01G 11/06* (2013.01); *H01G 11/38* (2013.01); *H01M 4/0404* (2013.01); *H01M 4/0471* (2013.01); *H01M 4/133* (2013.01); *H01M 4/134* (2013.01); *H01M 4/1393* (2013.01); *H01M 4/1395* (2013.01); *H01M 4/386* (2013.01); *H01M 4/587* (2013.01); *C08L 2312/08* (2013.01); *H01M 10/05* (2013.01); *H01M 10/052* (2013.01); *Y02E 60/13* (2013.01); *Y02T 10/7022* (2013.01)

(58) Field of Classification Search
CPC .. H01M 4/0404; H01M 4/0471; H01M 4/133; H01M 4/134; H01M 4/386; H01M 4/587; H01M 4/622; H01M 4/1393; H01M 4/1395; H01M 10/05; H01M 10/052; H01G 11/06; H01G 11/38; C08F 8/32; C08F 8/40; C08F 8/42; C08F 20/02; C07C 211/55
See application file for complete search history.

(56) References Cited

U.S. PATENT DOCUMENTS

| | | | |
|---|---|---|---|
| 2007/0087267 A1 | 4/2007 | Kim et al. | |
| 2009/0136845 A1 | 5/2009 | Choi et al. | |
| 2013/0089776 A1 | 4/2013 | Wata et al. | |
| 2013/0184385 A1 | 7/2013 | Ogihara | |
| 2013/0273423 A1 | 10/2013 | Jeong et al. | |
| 2013/0323587 A1* | 12/2013 | Kose | H01M 4/386 429/211 |
| 2014/0154562 A1* | 6/2014 | Fukuchi | H01M 10/052 429/211 |
| 2014/0312268 A1 | 10/2014 | Lim | |

FOREIGN PATENT DOCUMENTS

| | | | |
|---|---|---|---|
| CN | 102959786 A | 3/2013 | |
| CN | 103053048 A | 4/2013 | |
| CN | 103456964 A | 12/2013 | |

(Continued)

OTHER PUBLICATIONS

Machine Translation of JP 2015-103449 A (Year: 2015).*
Communication dated Aug. 21, 2017 from the German Patent and Trademark Office in counterpart application No. 11 2015 004 779.4.
Communication dated Sep. 29, 2017 from the United States Patent and Trademark Office in counterpart U.S. Appl. No. 15/519,977.
Communication dated Feb. 27, 2018, from the State Intellectual Property Office of People's Republic of China in counterpart Application No. 201580056342.8.

(Continued)

*Primary Examiner* — Robert S Carrico
(74) *Attorney, Agent, or Firm* — Sughrue Mion, PLLC

(57) ABSTRACT

A polymer compound, which is used as a binder for a negative electrode of an electricity storage device, is obtained by condensation of a vinyl polymer that contains a carboxyl group and a third compound that is selected from among an aromatic multifunctional amine, phosphorous acid, phosphorous acid ester, trialkoxysilane, and phosphoric acid.

8 Claims, No Drawings

(56) References Cited

U.S. PATENT DOCUMENTS

JP 2003-3031 1/2003
JP 2009-80971 4/2009
JP 2009-135103 6/2009
JP 2009-256570 11/2009
JP 2013-131368 7/2013
JP 2014-110234 6/2014
JP 2015-103449 6/2015
JP 2015103449 * 6/2015
WO 2010/098380 9/2010

OTHER PUBLICATIONS

Notice of Allowance dated Jan. 16, 2018, which issued during the prosecution of U.S. Appl. No. 15/519,977.
Translation of International Preliminary Report on Patentability dated May 30, 2017 in counterpart International Application No. PCT/JP2015/080632.

* cited by examiner

POLYMER COMPOUND, INTERMEDIATE COMPOSITION, NEGATIVE ELECTRODE, ELECTRICITY STORAGE DEVICE, SLURRY FOR NEGATIVE ELECTRODES, METHOD FOR PRODUCING POLYMER COMPOUND, AND METHOD FOR PRODUCING NEGATIVE ELECTRODE

CROSS REFERENCE TO RELATED APPLICATIONS

This application is a National Stage of International Application No. PCT/JP2015/080632, filed on Oct. 30, 2015, which claims priority from Japanese Patent Application No. 2014-238097, filed on Nov. 25, 2014, the contents of all of which are incorporated herein by reference in their entirety.

TECHNICAL FIELD

The present invention relates to a polymer compound for use as a binder for a negative electrode of an electrical storage device, an intermediate composition for the polymer compound, a negative electrode, an electrical storage device, a slurry for a negative electrode, a method for producing a polymer compound, and a method for producing a negative electrode.

BACKGROUND ART

Numerous mobile devices such as mobile phones and notebook-sized personal computers are utilized as a product using a rechargeable battery. The rechargeable battery is also attracting attention as a large-sized battery for an electric vehicle.

An electrode of the rechargeable battery is constituted by: a collector made of a metallic material such as copper or aluminum; and an active material layer bound onto the collector. The active material layer generally contains a binding agent as a binder for an electrode for binding an active material to the collector. In recent years, attempts have been made to use a carboxy group-containing vinyl polymer such as polyacrylic acid as a binder for an electrode. Patent Document 1 discloses a binder for an electrode, the binder containing a lithium salt of polyacrylic acid or a sodium salt of polyacrylic acid. Patent Document 2 discloses a binder for an electrode, the binder containing polyacrylic acid and polyethyleneimine. Patent Document 3 discloses a binder for an electrode, the binder containing polyacrylic acid and an amine compound.

PRIOR ART DOCUMENTS

Patent Documents

Patent Document 1: Japanese Laid-Open Patent Publication No. 2009-080971
Patent Document 2: Japanese Laid-Open Patent Publication No. 2009-135103
Patent Document 3: Japanese Laid-Open Patent Publication No. 2003-003031

SUMMARY OF THE INVENTION

Problems that the Invention is to Solve

The present researchers have found that a polymer compound obtained by condensing a carboxy group-containing vinyl polymer, an aromatic multifunctional amine, and a third compound selected from phosphorous acid, phosphorous acid ester, trialkoxysilane, and phosphoric acid is useful as a binder for a negative electrode of an electrical storage device such as a rechargeable battery. Accordingly, it is an objective of the present invention to provide a polymer compound useful as a binder for a negative electrode of an electrical storage device and to provide an intermediate composition for obtaining the polymer compound. Another objective of the present invention is to provide a negative electrode, an electrical storage device, and slurry for a negative electrode each using the polymer compound as a negative electrode binder. Still another objective of the present invention is to provide a method for producing the polymer compound and a method for producing a negative electrode.

Means for Solving the Problems

To achieve the foregoing objective and in accordance with a first aspect of the present invention, a polymer compound for use as a binder for a negative electrode of an electrical storage device is provided. The polymer compound is a compound obtained by condensing a carboxy group-containing vinyl polymer, an aromatic multifunctional amine, and a third compound selected from phosphorous acid, phosphorous acid ester, trialkoxysilane, and phosphoric acid.

To achieve the foregoing objective and in accordance with a second aspect of the present invention, a polymer compound for use as a binder for a negative electrode of an electrical storage device is provided. At least one selected from a phosphoric acid group, a phosphoric acid ester group, and a trialkoxysilane groups is added to a carboxy group in a polymer compound obtained by condensing a carboxy group-containing vinyl polymer and an aromatic multifunctional amine.

In the above described polymer compound, the aromatic multifunctional amine is preferably a multifunctional amine represented by the following formula (1), wherein Y represents a straight chain alkyl group having 1 to 4 carbon atoms, a phenylene group, or an oxygen atom, R1 and R2 each independently represent one or more hydrogen atoms, methyl groups, ethyl groups, trifluoromethyl groups, or methoxy groups.

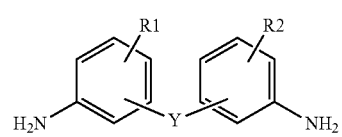

To achieve the foregoing objective and in accordance with a third aspect of the present invention, an intermediate composition for a polymer compound for use as a binder for a negative electrode of an electrical storage device is provided. The intermediate composition contains a carboxy group-containing vinyl polymer, an aromatic multifunctional amine, a third compound selected from phosphorous acid, phosphorous acid ester, trialkoxysilane, and phosphoric acid, and a nonaqueous solvent.

To achieve the foregoing objective and in accordance with a fourth aspect of the present invention, a method for producing a polymer compound for use as a binder for a negative electrode of an electrical storage device is provided. The method includes condensing a carboxy group-containing vinyl polymer, an aromatic multifunctional amine, and a third compound selected from phosphorous acid, phosphorous acid ester, trialkoxysilane, and phosphoric acid.

In the above described method for producing a polymer compound, the third compound is preferably at least one selected from phosphorous acid, phosphorous acid ester, and trialkoxysilane, and the method preferably further includes mixing the vinyl polymer and the aromatic multifunctional amine, and thereafter mixing the third compound.

The above described method for producing a polymer compound preferably includes mixing the vinyl polymer and the aromatic multifunctional amine and heating the resultant mixture at a temperature of 40° C. to 140° C., and thereafter mixing the third compound and heating the resultant mixture at a temperature of 150° C. to 230° C.

In the above described method for producing a polymer compound the third compound is preferably phosphoric acid, and the method preferably further includes heating the vinyl polymer, the aromatic multifunctional amine, and the third compound at a temperature of 40° C. to 140° C. and thereafter heating the vinyl polymer, the aromatic multifunctional amine, and the third compound at a temperature of 150° C. to 230° C.

To achieve the foregoing objective and in accordance with a fifth aspect of the present invention, a negative electrode of an electrical storage device is provided. The negative electrode includes a binder for a negative electrode including the above described polymer compound, and a negative electrode active material. The negative electrode active material is at least one selected from carbon-based materials capable of intercalating and deintercalating lithium, elements capable of producing alloy with lithium, and compounds including an element capable of producing alloy with lithium.

In the above described negative electrode, the negative electrode active material is preferably at least one selected from: silicon materials obtained from $CaSi_2$ through decalcification reaction; Si; and $SiO_v$ (0>v >2) (0<v<2).

To achieve the foregoing objective and in accordance with a sixth aspect of the present invention, an electrical storage device is provided that includes the above described the negative electrode and a nonaqueous electrolyte.

To achieve the foregoing objective and in accordance with a seventh aspect of the present invention, a slurry for a negative electrode for use in producing a negative electrode of an electrical storage device is provided. The slurry includes the above described intermediate composition, a negative electrode active material, and a solvent. The negative electrode active material is at least one selected from carbon-based materials capable of intercalating and deintercalating lithium, elements capable of producing alloy with lithium, and compounds including an element capable of producing alloy with lithium.

To achieve the foregoing objective and in accordance with an eighth objective of the present invention, a method for producing a negative electrode of an electrical storage device is provided. The method includes forming a negative electrode active material layer to a collector using the above described slurry for a negative electrode.

In the above described method for producing a negative electrode, the slurry for a negative electrode preferably includes at least one selected from: silicon materials obtained from $CaSi_2$ through decalcification reaction; Si; and $SiO_v$ (0<v<2).

To achieve the foregoing objective and in accordance with a ninth aspect of the present invention, a polymer compound for use as a binder for a negative electrode of an electrical storage device is provided. The polymer compound includes a chain structure constituted by a carboxy group-containing vinyl polymer and a crosslinked structure connecting carboxylic acid side chains in the chain structure or between the chain structures. The crosslinked structure is at least one crosslinked structure selected from the following formulas (3) to (5), and at least one selected from a phosphoric acid group, a phosphate group, and a trialkoxysilane group is added to a carboxy group contained in the chain structure.

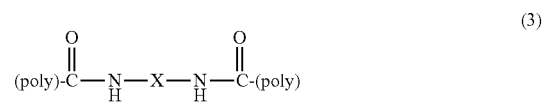

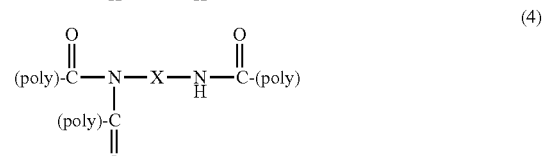

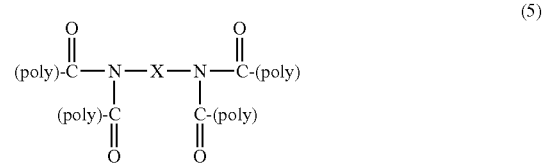

To achieve the foregoing objective and in accordance with a tenth aspect of the present invention, a binder for a negative electrode is provided that includes the above described polymer compound.

To achieve the foregoing objective and in accordance with an eleventh aspect of the present invention, a method for producing a negative electrode of an electrical storage device is provided. The method includes an active material layer-forming step of forming a negative electrode active material layer on a collector using a mixture including an intermediate composition and a negative electrode active material, and a condensation step of condensing the vinyl polymer and the aromatic multifunctional amine by heat-treating the negative electrode active material layer.

Effects of the Invention

According to the present invention, properties of an electrical storage device are improved.

MODES FOR CARRYING OUT THE INVENTION

First Embodiment

A first embodiment of the present invention will now be described.

A polymer compound according to the present embodiment is a compound obtained by condensing a carboxy group-containing vinyl polymer (A), an aromatic multifunctional amine (B), and a third compound (C).

Examples of the carboxy group-containing vinyl polymer (A) include polyacrylic acid, polymethacrylic acid, copolymers of acrylic acid and methacrylic acid, and copolymers of at least one of acrylic acid and methacrylic acid and an additional vinyl monomer. Examples of the additional vinyl monomer include compounds having a vinyl group, a vinylene group, or a vinylidene group, such as acrylic acid ester, methacrylic acid ester, butene, isobutene, maleic acid, itaconic acid, acrylamide, methacrylamide, styrene, acrylonitrile, and methacrylonitrile. These additional vinyl monomers may be used singly or in combinations of two or more. In the following description, the carboxy group-containing vinyl polymer (A) will be simply referred to as a vinyl polymer (A).

The weight average molecular weight of the vinyl polymer (A) is not particularly limited, and is preferably in a range of, for example, 10,000 to 2,000,000, more preferably in a range of 25,000 to 1,800,000, and still more preferably in a range of 50,000 to 1,500,000.

In the case where a conventional polymer compound such as polyamide-imide is used as a binder for a negative electrode, there is a tendency that the cyclability of an electrical storage device is lowered as the weight average molecular weight of the polymer compound is lowered. In contrast, in the case where the polymer compound according to the present embodiment is used as a binder for a negative electrode, even when the weight average molecular weight of the carboxy group-containing vinyl polymer that constitutes the polymer compound is lowered, the cyclability of an electrical storage device is maintained. Therefore, as the carboxy group-containing vinyl polymer, a low-molecular weight vinyl polymer having a molecular weight of, for example, 250,000 or lower or 100,000 or lower is used effectively.

The aromatic multifunctional amine (B) is a compound that has in the molecular structure an aromatic ring structure to which two or more amino groups are bound. Examples of the aromatic multifunctional amine (B) include a compound having a structure represented by the following formula (1).

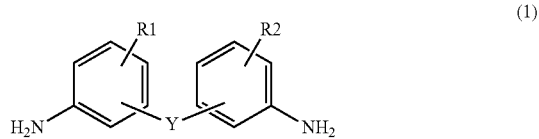

(1)

In formula (1), Y represents a straight chain alkyl group having 1 to 4 carbon atoms, a phenylene group, or an oxygen atom. The binding position of Y in each benzene ring may be an ortho position, a meta position, or a para position to an amino group.

In the case where Y represents a straight chain alkyl group or a phenylene group, a substituent may be bound to a carbon atom that constitutes the structure of Y. Examples of the substituent to be bound to a carbon atom that constitutes the straight chain alkyl group include a methyl group, an ethyl group, a fluoromethyl group, a difluoromethyl group, a trifluoromethyl group, a methoxy group, an ethoxy group, and an oxo group. One or more of these substituents may be bound. The number of substituents to be bound to one carbon atom may be one or two. Furthermore, the substituent to be bound to a carbon atom that constitutes the straight chain alkyl group or the phenylene group may be an amino group or a substituent containing an amino group, and in that case, the multifunctional amine is a multifunctional amine having 3 or more amino groups.

In formula (1), R1 and R2 each independently represent one or more hydrogen atoms, methyl groups, ethyl groups, trifluoromethyl groups, or methoxy groups. In the case where R1 represents a methyl group, an ethyl group, a trifluoromethyl group, or a methoxy group, the binding position of R1 may be any of an ortho position, a meta position, or a para position to an amino group. The same applies to R2.

Examples of the multifunctional amine in which Y represents a straight chain alkyl group include 3,3'-diaminodiphenylmethane, 4,4'-diaminodiphenylmethane, 3,4'-diaminodiphenylmethane, 4,4'-ethylene dianiline, 4,4'-diamino-3,3'-dimethyldiphenylmethane, 1,1-bis(4-aminophenyl)cyclohexane, 9,9-bis(4-aminophenyl)fluorene, 2,2'-bis(4-aminophenyl)hexafluoropropane, 4,4'-diaminobenzophenone, 4,4'-methylenebis(2-ethyl-6-methylaniline), and pararosaniline. Examples of the multifunctional amine in which Y represents a phenylene group include 1,3,5-tris(4-aminophenyl)benzene. Examples of the multifunctional amine in which Y represents an oxygen atom include 4,4'-diaminodiphenyl ether. 1,3,5-tris(4-aminophenyl)benzene and pararosaniline are a trifunctional amine having 3 amino groups. The multifunctional amines may be used singly or in combinations of two or more Examples of the aromatic multifunctional amine (B) other than the compound having a structure represented by formula (1) include 1,2-diaminobenzene, 1,3-diaminobenzene, 1,4-diaminobenzene, 2,4-diaminotoluene, 2,5-diaminotoluene, 3,4-diaminotoluene, 3,4-diaminobenzoic acid, 3,5-diaminobenzoic acid, 1,5-diaminonaphthalene, and 1,8-diaminonaphthalene. The aromatic multifunctional amines may be used singly or in combinations of two or more.

The compounding ratio of the aromatic multifunctional amine (B) is set according to the number of amino groups in the aromatic multifunctional amine (B). That is, the compounding ratio is set such that the number of carboxy groups in the vinyl polymer (A) is larger than the number of amino groups in the aromatic multifunctional amine (B). In other words, the compounding ratio is set such that the carboxy groups in the vinyl polymer (A) are 1 equivalent or more in relation to 1 equivalent of amino groups in the aromatic multifunctional amine (B). It is preferable that the ratio (carboxy groups/amino groups) of the number of carboxy groups in the vinyl polymer (A) to the number of amino groups in the aromatic multifunctional amine (B) be in a range of 1.5/1 to 15/1, and more preferably in a range of 2/1 to 10/1.

As the third compound (C), at least one selected from phosphorous acid, phosphorous acid ester, and trialkoxysilane is used. Examples of the phosphorous acid ester include alkyl phosphate ester having a straight chain or branched chain alkyl group having 1 to 4 carbon atoms, such as dimethyl phosphite, trimethyl phosphite, diethyl phosphite, and triethyl phosphite.

Examples of the trialkoxysilane include a compound having a structure represented by formula (2).

(2)

In formula (2), R3 to R5 each independently represent a straight chain or branched chain alkyl group having 1 to 4 carbon atoms. Examples of the compound having a structure represented by formula (2) include trimethoxysilane and triethoxysilane.

Among the third compounds (C), phosphorous acid ester and trialkoxysilane are preferably used. These compounds are excellent in compatibility with polymer compounds such as vinyl polymers (A). Therefore, when these compounds are mixed with a vinyl polymer (A), the aggregation of the vinyl polymer (A) is hard to occur and a larger number of the third compounds (C) are easily condensed.

It is preferable that the compounding ratio of the third compound (C) be in a range of 1/100 to 1/10 equivalent in relation to 1 equivalent of the vinyl polymer (A) in terms of the monomer. Particularly, in the case where the third compound is phosphorous acid, it is preferable that the compounding ratio of the third compound (C) be in a range of 1/100 to 1/20 equivalent in relation to 1 equivalent of the vinyl polymer (A) in terms of the monomer, and more preferably in a range of 1/75 to 1/30 equivalent. In the case where the third compound is a phosphorous acid ester or a trialkoxysilane, it is preferable that the compounding ratio of the third compound (C) be in a range of 1/100 to 1/10 equivalent in relation to 1 equivalent of the vinyl polymer (A) in terms of the monomer, and more preferably in a range of 1/75 to 1/20 equivalent. In the case where the vinyl polymer (A) is a copolymer, the compounding ratio of the third compound (C) is set in terms of a monomer determined when all the constitutional units that constitute the vinyl polymer are assumed to be the same.

It is preferable that the compounding ratio of the third compound (C) be in a range of 1/100 to 1/5 equivalent in relation to 1 equivalent of the carboxy groups in the vinyl polymer (A), and more preferably in a range of 1/50 to 1/10 equivalent.

There is a tendency that the adhesiveness of the polymer compound to an active material or a collector is improved as the compounding ratio of the third compound (C) increases. In contrast, there is a tendency that the property of the polymer compound such as flexibility, strength, or extensibility becomes easy to ensure as the compounding ratio of the third compound (C) decreases. By setting the compounding ratio of the third compound (C) in the above-described range, the adhesiveness of the polymer compound to an active material or a collector is improved, and the flexibility, strength, or extensibility of the polymer compound can be ensured.

The polymer compound according to the present embodiment is obtained through a first mixing step of mixing the vinyl polymer (A) and the aromatic multifunctional amine (B) in a solvent, a second mixing step of further mixing the third compound (C) with the first intermediate composition obtained in the first mixing step, and a heating step of subjecting the second intermediate composition obtained in the second mixing step to heating treatment.

The first mixing step is a step of obtaining the first intermediate composition in which the vinyl polymer (A), the aromatic multifunctional amine (B), and the solvent are mixed. As the solvent for use in the first mixing step, the solvent in which the vinyl polymer (A) and the aromatic multifunctional amine (B) are dissolved can be selected and used appropriately. Particularly, it is preferable to use a nonaqueous solvent such as N-methyl-2-pyrrolidone, dimethylformamide, dimethylacetamide, dimethyl sulfoxide, propylene carbonate, γ-butyrolactone, ethanol, and propanol from the viewpoint of improving solubility.

The second mixing step is a step of mixing the third compound (C) with the first intermediate composition, thereby obtaining the second intermediate composition in which the third compound (C) is condensed with a carboxy group in the vinyl polymer (A) contained in the first intermediate composition. The condensation reaction in the second mixing step progresses through stirring at room temperature; however, a catalyst may be added to the reaction system or heat treatment may be conducted to increase the reaction rate of the condensation reaction if necessary.

The heating step is a step of subjecting the second intermediate composition to heating treatment, thereby condensing the vinyl polymer (A) and the aromatic multifunctional amine (B) contained in the second intermediate composition. It is preferable that the heating temperature in the heating step be in a range of 150° C. to 230° C., and more preferably in a range of 180° C. to 200° C. By raising the heating temperature, an imide bond moiety becomes easy to form as a condensation moiety between a carboxy group and an amino group in addition to an amide bond moiety and the ratio of the imide bond moiety in the condensation moiety can be increased. By raising the heating temperature, there is a tendency that a property (cyclability) of an electrical storage device can be enhanced in the case where the polymer compound according to the present embodiment is used as a binder for a negative electrode.

When the second intermediate composition is heated, a catalyst may be added to the intermediate composition to make the condensation reaction for forming an amide bond and an imide bond to progress or to increase the reaction rate of the condensation reaction. As the catalyst, dehydration catalysts such as, for example, carbodiimide, diphenylphosphoryl azide, and a BOP reagent can be used effectively.

It is preferable that the second intermediate composition to be subjected to the heating step be an intermediate composition to which preheating treatment has been conducted in the first mixing step. It is preferable that the temperature in the preheating treatment be in a range of 40° C. to 140° C., and more preferably in a range of 60° C. to 130° C. By the preheating treatment, the vinyl polymer (A) and the aromatic multifunctional amine (B) associate with each other to form a state where the condensation reaction between a carboxy group and an amino group easily progresses. Thus, the condensation reaction progresses efficiently in the heating step. The condensation reaction between the carboxy group and the amino group may progress partially to form an amide bond moiety and an imide bond moiety by the preheating treatment.

In the case where the second intermediate composition to which the preheating treatment has been conducted is used, it is preferable to conduct the heating step in a state where the solvent contained in the second intermediate composition is removed. In that case, the condensation reaction between the vinyl polymer (A) and the aromatic multifunctional amine (B) becomes easy to progress.

The polymer compound in which the vinyl polymer (A), the aromatic multifunctional amine (B), and the third compound (C) are condensed is obtained through the heating step. It is considered that at least one of the amide bond and the imide bond is formed between a carboxy group in the vinyl polymer (A) and an amino group in the aromatic multifunctional amine (B), so that the polymer compound has a crosslinked structure in which the vinyl polymers (A) are crosslinked. A carboxy group in the vinyl polymer (A) and the third compound (C) are condensed to form an end structure derived from the third compound (C) in a carboxy group. That is, a phosphoric acid group in the case where the third compound (C) is phosphorous acid, a phosphoric acid ester group in the case where the third compound (C) is a phosphorous acid ester, or a trialkoxysilane group in the case where the third compound (C) is a trialkoxysilane is added to a carboxy group in the vinyl polymer (A).

In other words, the polymer compound has a chain structure constituted by the vinyl polymer (A), a crosslinked structure connecting carboxylic acid chains within the chain structure or between the chain structures, and an end structure derived from the third compound (C) in some of free carboxy groups. The crosslinked structure is at least one crosslinked structure selected from the following formulas (3) to (5).

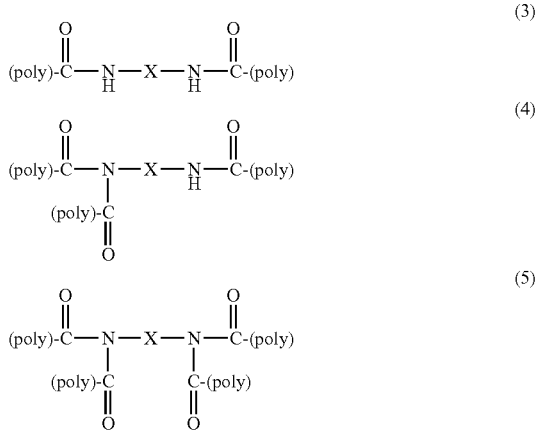

In formulas (3) to (5), "poly" represents a chain structure constituted by a vinyl polymer (A). In formulas (4) and (5) having an imide structure, the two carbonyl groups that constitute one imide structure may be carbonyl groups each bound to a different chain structure, or may be carbonyl groups each bound to the same chain structure. For example, in the case where the two carbonyl groups that constitute an imide structure are carbonyl groups bound to adjacent carbon atoms in the same chain structure, a maleimide structure is formed as the imide structure.

In formulas (3) to (5), X represents a structure derived from the aromatic multifunctional amine (B), and, for example, in the case where the aromatic multifunctional amine (B) is a multifunctional amine represented by formula (1), X represents a structure represented by the following formula (6).

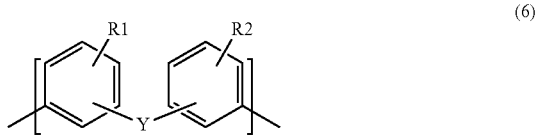

In formula (6), Y represents a straight chain alkyl group having 1 to 4 carbon atoms, a phenylene group, or an oxygen atom. The binding position of Y in each benzene ring may be any of an ortho position, a meta position, and a para position to an amino group. In formula (6), Y has a structure that conforms to Y in formula (1).

In formula (6), R1 and R2 each independently represent one or more hydrogen atoms, methyl groups, ethyl groups, trifluoromethyl groups, or methoxy groups. In the case where R1 represents a methyl group, an ethyl groups, a trifluoromethyl group, or a methoxy group, the binding position of R1 may be any of an ortho position, a meta position, and a para position to an amino group. The same applies to R2. R1 and R2 in formula (6) have a structure that conforms to R1 and R2 in formula (1), respectively.

It is preferable that the polymer compound have both the amide bond moiety and the imide bond moiety in the crosslinked structure thereof. That is, it is preferable that the polymer compound have at least the crosslinked structure of formula (3) and the crosslinked structure of formula (5), or at least the crosslinked structure of formula (4).

Next, an example of the method for producing a negative electrode using the polymer compound according to the present embodiment as a binder for a negative electrode will be described.

First, a slurry is prepared by mixing a negative electrode active material, a binder for a negative electrode, and a solvent. When the slurry is prepared, an additional component such as a conductive aid may further be mixed if necessary.

As the negative electrode active material, known materials for use as a negative electrode active material of an electrical storage device such as a rechargeable battery, for example, carbon-based materials, elements capable of producing alloy with lithium, and compounds containing an element capable of producing alloy with lithium, can be used.

As the carbon-based material, for example, carbon-based materials capable of intercalating and deintercalating lithium can be used, and specific examples thereof include hardly graphitizable carbon, natural graphite, artificial graphite, cokes, graphites, glassy carbons, organic polymer compound-sintered bodies, carbon fibers, active carbon, and carbon blacks.

Examples of the element capable of producing alloy with lithium include Na, K, Rb, Cs, Fr, Be, Mg, Ca, Sr, Ba, Ra, Ti, Ag, Zn, Cd, Al, Ga, In, Si, Ge, Sn, Pb, Sb, and Bi. Among these, Si is particularly preferable.

Examples of the compound containing an element capable of producing alloy with lithium include compounds containing an element selected from Na, K, Rb, Cs, Fr, Be, Mg, Ca, Sr, Ba, Ra, Ti, Ag, Zn, Cd, Al, Ga, In, Si, Ge, Sn, Pb, Sb, and Bi. Among these, silicon-based materials that are compounds containing silicon are particularly preferable.

Examples of the silicon-based material include $SiB_4$, $SiB_6$, $Mg_2Si$, $Ni_2Si$, $TiSi_2$, $MoSi_2$, $CoSi_2$, $NiSi_2$, $CaSi_2$, $CrSi_2$, $Cu_5Si$, $FeSi_2$, $MnSi_2$, $NbSi_2$, $TaSi_2$, $VSi_2$, $WSi_2$, $ZnSi_2$, $SiC$, $Si_3N_4$, $Si_2N_2O$, $SiO_v$ ($0<V\leq2$), $SnSiO_3$, and $LiSiO$. Among these, $SiO_v$ ($0<V\leq2$) is particularly preferable.

A silicon material disclosed in International Publication No. WO 2014/080608 and obtained from $CaSi_2$ through decalcification reaction can also be used as the silicon-based material. The silicon material is a silicon material obtained by, for example, subjecting a layered polysilane which is obtained by treating $CaSi_2$ with an acid (for example, hydrochloric acid or hydrogen fluoride) to decalcification (for example, heating treatment at 300° C. to 1,000° C.). As the negative electrode active material, the above-described materials may be used singly or in combinations of two or more. It is particularly preferable that the polymer compound according to the present embodiment be used in combination with a silicon-based material that is a negative electrode active material for which the degree of expansion and contraction during charge and discharge is large.

As the negative electrode active material, the above-described materials may be used singly or in combinations of two or more.

As a binder for a negative electrode to be mixed with the slurry, the second intermediate composition is used. In the following description, the second intermediate composition will be simply referred to as an intermediate composition.

The binder for a negative electrode may be used together with an additional binder for a negative electrode. Examples of the additional binder for a negative electrode include polyvinylidene fluoride, polytetrafluoroethylene, styrene-butadiene rubber, polyimide, polyamide-imide, carboxymethyl cellulose, polyvinyl chloride, methacrylic resins, polyacrylonitrile, modified polyphenylene oxides, polyethylene oxide, polyethylene, polypropylene, polyacrylic acid, and phenol resins. These additional binders for a negative electrode may be used singly or in combinations of two or more. In the case where the additional binder for a negative electrode is used together, it is preferable that the solid content of the intermediate composition contained be 1% by mass or more in relation to the total solid content of the binder for a negative electrode, and more preferably 10% by mass or more.

The compounding ratio (negative electrode active material:binder for negative electrode) of the negative electrode active material to the binder for a negative electrode in terms of the mass ratio can be set appropriately according to the kind of the negative electrode active material and the binder for a negative electrode. It is preferable that the compounding ratio be in a range of, for example, 5:3 to 99:1, more preferably in a range of 3:1 to 97:3, and still more preferably in a range of 16:3 to 95:5.

As a solvent, known solvents for use in producing an electrode of an electrical storage device such as a rechargeable battery can be used appropriately according to the kind of the negative electrode active material and the binder for a negative electrode. Specific examples of the solvent include N-methyl-2-pyrollidone, methanol, and methyl isobutyl ketone.

Subsequently, the slurry is applied to a collector to form a negative electrode active material layer made from the slurry on the surface of the collector. Thereafter, solvents (solvent for slurry and solvent contained in the intermediate composition) contained in the negative electrode active material layer are removed to dry the negative electrode active material layer. Heating treatment is then conducted at a temperature of 150° C. to 230° C. to cure the negative electrode active material layer. By this heating treatment, the vinyl polymer (A) and the aromatic multifunctional amine (B) contained in the intermediate composition are condensed to form the polymer compound according to the present embodiment in the negative electrode active material layer. The heating treatment can be conducted in a state where the solvents are contained in the negative electrode active material layer; however, it is more preferable to conduct the heating treatment in a state where the negative electrode active material layer has been dried.

Known metallic materials for use as a collector for a negative electrode of an electrical storage device such as a rechargeable battery can be used as the collector. Specific examples of the metallic material that can be used as the collector include silver, copper, gold, aluminum, magnesium, tungsten, cobalt, zinc, nickel, iron, platinum, tin, indium, titanium, ruthenium, tantalum, molybdenum, and stainless steel.

The negative electrode using the polymer compound according to the present embodiment as a binder for a negative electrode can be used effectively for a nonaqueous type electrical storage device including a nonaqueous electrolyte as an electrolyte. Examples of the electrical storage device include rechargeable batteries, electric double layer capacitors, and lithium ion capacitors. These electrical storage devices are useful as a nonaqueous rechargeable battery for driving a motor of electric vehicles and hybrid vehicles or as a nonaqueous rechargeable battery used for personal computers, mobile communication devices, home electric appliances, office devices, and industrial devices.

Next, advantages of the present embodiment will be described.

(1) The polymer compound according to the present embodiment is a polymer compound obtained by condensing a carboxy group-containing vinyl polymer, an aromatic multifunctional amine, and a third compound that is at least one selected from phosphorous acid, phosphorous acid ester, and trialkoxysilane. The polymer compound according to the present embodiment is a polymer compound in which at least one selected from a phosphoric acid group, phosphoric acid ester groups, and trialkoxysilane groups is added to a carboxy group in a polymer compound obtained by condensing a carboxy group-containing vinyl polymer and an aromatic multifunctional amine. The polymer compound according to the present embodiment is a polymer compound obtained by subjecting an intermediate composition (second intermediate composition) containing: a carboxy group-containing vinyl polymer; an aromatic multifunctional amine; a third compound selected from phosphorous acid, phosphorous acid ester, trialkoxysilane; and a non-aqueous solvent to heating treatment at a temperature of 150° C. to 230° C.

The polymer compound according to the present embodiment is useful as a binder for a negative electrode of an electrical storage device. By using the polymer compound according to the present embodiment as a binder for a negative electrode, the properties (initial efficiency and cyclability) of an electrical storage device can be enhanced.

Particularly, an end structure containing a phosphorus atom or a silicon atom that is derived from the third compound is introduced to a carboxy group that does not form a crosslinked structure. The end structure is superior in adhesiveness to a collector to carboxy groups. That is, in a binder for a negative electrode, the binder using a carboxy group as an adhesion site to the collector, the carboxy group may be bound to lithium in an electrolytic solution and may be eliminated as lithium carbonate. The elimination of a carboxy group brings about lowering of the adhesiveness of a binder for a negative electrode to a collector and peeling of the binder for a negative electrode from a collector. In contrast, when the end structure is introduced to a carboxy group in the above-described constitution, the elimination of a carboxy group is suppressed. Therefore, the adhesiveness between the binder for a negative electrode and a collector can be maintained for a long time, so that the cyclability of an electrical storage device is improved.

The polymer compound according to the present embodiment has a characteristic that the cyclability of an electrical storage device is easily maintained even in the case where the weight average molecular weight of a chain structure made of a carboxy group-containing vinyl polymer is lowered. Therefore, even in the case where the polymer compound is made to have a short chain structure moiety and a low molecular weight, the polymer compound can function effectively as a binder for a negative electrode. In the case where the polymer compound having a low molecular weight is used as a binder for a negative electrode, a slurry can be prepared with a smaller amount of solvent, and therefore the solid content ratio in the slurry can be set large. By setting the solid content ratio in the slurry large, the drying time for volatilizing the solvents from the negative electrode active material layer in producing a negative electrode is shortened to improve the productivity of the negative electrode. Accordingly, in the case where the polymer compound according to the present embodiment is used as a binder for a negative electrode, it is easy to improve the productivity of a negative electrode.

(2) The aromatic multifunctional amine is a multifunctional amine represented by the formula (1). In this multifunctional amine, two amino groups are each bound to a different aromatic ring connected to another aromatic ring by a moiety Y. Therefore, the motion such as rotation at the moiety Y is allowed, so that the elasticity of the polymer compound is improved. Thereby, the binder for a negative electrode using the polymer compound according to the present embodiment becomes easy to follow the change in volume due to the expansion and contraction accompanying the intercalation and deintercalation of lithium or the like. As a result, the properties of an electrical storage device are enhanced.

(3) The third compound is phosphorous acid, a phosphorous acid ester, or a trialkoxysilane. These compounds are compatible with the first intermediate composition in a state where the carboxy group-containing vinyl polymer and the aromatic multifunctional amine associate with each other. Therefore, the polymer compound can be obtained by adding the third compound after forming the first intermediate composition, so that a structure derived from the third compound can be introduced selectively to a carboxy group that does not form a crosslinked structure in the polymer compound. Thereby, the adhesiveness based on the end structure derived from the third compound is improved effectively and the cyclability of an electrical storage device is also improved.

Compounds having a structure similar to that of phosphorous acid, phosphorous acid ester, and trialkoxysilane include phosphoric acid. However, in the case where phosphoric acid is used in place of the third compound, the synthesis route of obtaining the polymer compound by adding the third compound after forming the first intermediate composition cannot be adopted due to the problem such as compatibility with the first intermediate composition. Therefore, it is difficult to introduce a structure derived from phosphoric acid selectively to a carboxy group that does not form a crosslinked structure in the polymer compound.

(4) The third compound is a phosphorous acid ester or a trialkoxysilane. The phosphorous acid ester and the trialkoxysilane are particularly excellent in compatibility with the first intermediate composition when compared with phosphorous acid, which is a compound that exhibits a high hydrophilic property. Therefore, a phosphoric acid ester and the trialkoxysilane can be compounded without excessively aggregating a vinyl polymer in the second mixing step even when the compounded amount is so large that the vinyl polymer aggregates in the case of phosphorous acid. That is, a larger amount of the third compound can be compounded in the case where the phosphoric acid ester and the trialkoxysilane are used than in the case where phosphorous acid is used. Thus, a larger number of the end structures derived from the third compound can be introduced to carboxy groups in the polymer compound. Thereby, the adhesiveness based on the end structure derived from the third compound is improved effectively and the cyclability of an electrical storage device is further enhanced.

Second Embodiment

A second embodiment of the present invention will now be described.

A polymer compound according to the present embodiment is a polymer compound obtained by condensing a carboxy group-containing vinyl polymer (A), an aromatic multifunctional amine (B), and a third compound (C).

The carboxy group-containing vinyl polymer (A) and the aromatic multifunctional amine (B) are the same as those in the first embodiment.

As the third compound, phosphoric acid is used.

It is preferable that the compounding ratio of the third compound (C) be in a range of 1/100 to 1/10 equivalent in relation to 1 equivalent of the vinyl polymer (A) in terms of the monomer, and more preferably in a range of 1/75 to 1/20 equivalent. In the case where the vinyl polymer (A) is a copolymer, the compounding ratio of the third compound (C) is set in terms of a monomer determined when all the constitutional units that constitute the vinyl polymer are assumed to be the same.

The polymer compound according to the present embodiment is obtained through a mixing step of mixing the vinyl polymer (A), the aromatic multifunctional amine (B), and the third compound (C) in a solvent, and a heating step of subjecting the intermediate composition obtained in the mixing step to heating treatment.

The mixing step is a step of obtaining an intermediate composition in which the vinyl polymer (A), the aromatic multifunctional amine (B), the third compound (C), and the solvent are mixed. As the solvent for use in the mixing step, the solvent in which the vinyl polymer (A) and the aromatic multifunctional amine (B) are dissolved can be selected and used appropriately. Particularly, it is preferable to use a nonaqueous solvent such as N-methyl-2-pyrrolidone, dimethylformamide, dimethylacetamide, dimethyl sulfoxide, propylene carbonate, γ-butyrolactone, ethanol, and propanol from the viewpoint of improving solubility.

The heating step is a step of subjecting the intermediate composition to heating treatment, thereby condensing the vinyl polymer (A), the aromatic multifunctional amine (B), and the third compound (C) contained in the intermediate composition. The polymer compound in which the vinyl polymer (A), the aromatic multifunctional amine (B), and the third compound (C) are condensed is obtained through the heating step.

It is preferable that the heating temperature in the heating step be in a range of 150° C. to 230° C., and more preferably in a range of 180° C. to 200° C. By raising the heating temperature, an imide bond moiety becomes easy to form as a condensation moiety between a carboxy group and an amino group in addition to an amide bond moiety and the ratio of the imide bond moiety in the condensation moiety can be increased. By raising the heating temperature, there is a tendency that a property (cyclability) of an electrical storage device such as a rechargeable battery can be enhanced in the case where the polymer compound according to the present embodiment is used as a binder for a negative electrode.

When the intermediate composition is heated, a catalyst may be added to the intermediate composition to make the condensation reaction for forming an amide bond and an imide bond to progress or to increase the reaction rate of the condensation reaction. As the catalyst, dehydration catalysts such as, for example, carbodiimide, diphenylphosphoryl azide, and a BOP reagent can be used effectively.

It is preferable that the intermediate composition to be subjected to the heating step be an intermediate composition to which preheating treatment has been conducted in the mixing step. It is preferable that the temperature in the preheating treatment be in a range of 40° C. to 140° C., and more preferably in a range of 60° C. to 130° C. By the preheating treatment, the vinyl polymer (A) and the aromatic multifunctional amine (B) associate with each other to form a state where the condensation reaction between a carboxy group and an amino group easily progresses. Thus, the condensation reaction progresses efficiently in the heating step. The condensation reaction between the carboxy group and the amino group may progress partially to form an amide bond moiety and an imide bond moiety by the preheating treatment.

In the case where the intermediate composition to which the preheating treatment has been conducted is used, it is preferable to conduct the heating step in a state where the solvent contained in the intermediate composition is removed. In that case, the condensation reaction between the vinyl polymer (A) and the aromatic multifunctional amine (B) becomes easy to progress.

Like the polymer compound according to the first embodiment, the polymer compound according to the present embodiment can be used as a binder for a negative electrode to produce a negative electrode. As in the case of the first embodiment, the negative electrode using the polymer compound according to the present embodiment can be used effectively for a nonaqueous type electrical storage device including a nonaqueous electrolyte as an electrolyte.

Next, advantages of the present embodiment will be described.

(5) The polymer compound according to the present embodiment is a polymer compound obtained by condensing a carboxy group-containing vinyl polymer, an aromatic multifunctional amine, and phosphoric acid. The polymer compound according to the present embodiment is a polymer compound obtained by subjecting an intermediate composition containing: a carboxy group-containing vinyl polymer; an aromatic multifunctional amine; phosphoric acid; and a nonaqueous solvent to heating treatment at a temperature of 150° C. to 230° C.

The polymer compound according to the present embodiment is useful as a binder for a negative electrode of an electrical storage device. By using the polymer compound according to the present embodiment as a binder for a negative electrode, the properties (initial efficiency and cyclability) of an electrical storage device can be enhanced.

EXAMPLES

Hereinafter, examples that further substantiate the embodiments will be described.
<Test 1>
Battery properties were evaluated in the case where polymer compounds using phosphorous acid or a trialkoxysilane as the third compound were used. Hereinafter, polyacrylic acid is denoted as PAA, N-methyl-2-pyrrolidone is denoted as NMP, and polyamide-imide is denoted as PAI.

Example 1: PAA+4,4'-Diaminodiphenylmethane+ Phosphorous Acid

PAA having a weight average molecular weight of 800,000 was dissolved in NMP to prepare a 10% by mass PAA/NMP solution, and 6 ml (9.5 mmol in terms of monomer for PAA) of the PAA/NMP solution was taken out and placed in a flask under a nitrogen atmosphere. Separately from the solution, 0.1 g (0.5 mmol) of 4,4'-diaminodiphenylmethane was dissolved in 0.4 ml of NMP to prepare an amine/NMP solution. The whole amount of the amine/NMP solution was dropped into the PAA/NMP solution while stirring the PAA/NMP solution in the flask, and stirring was continued at room temperature for 30 minutes. Thereafter, heating treatment (preheating treatment) was conducted at 130° C. for 3 hours with a Dean-Stark apparatus. To the treated solution, 15 mg (0.18 mmol) of phosphorous acid was added, and the resultant mixture was stirred at room temperature for 6 hours to obtain an intermediate composition (second intermediate composition) of Example 1 in a state of an NMP solution.

Example 2: PAA+4,4'-Diaminodiphenylmethane+ Triethoxysilane

PAA having a weight average molecular weight of 800,000 was dissolved in NMP to prepare a 10% by mass PAA/NMP solution, and 6 ml (9.5 mmol in terms of monomer for PAA) of the PAA/NMP solution was taken out and placed in a flask under a nitrogen atmosphere. Separately from the solution, 0.1 g (0.5 mmol) of 4,4'-diaminodiphenylmethane was dissolved in 0.4 ml of NMP to prepare an amine/NMP solution. The whole amount of the amine/NMP solution was dropped into the PAA/NMP solution while stirring the PAA/NMP solution in the flask, and stirring was continued at room temperature for 30 minutes. Thereafter, heating treatment (preheating treatment) was conducted at 130° C. for 3 hours with a Dean-Stark apparatus. To the treated solution, 20 µl (0.11 mmol) of triethoxysilane was added, and the resultant mixture was stirred at room temperature for 12 hours to prepare an intermediate composition (second intermediate composition) of Example 2 in a state of an NMP solution.

As Reference Example, a polymer compound obtained by condensing PAA and 4,4'-diaminodiphenylmethane was synthesized.

Reference Example 1: PAA+4,4'-Diaminodiphenylmethane

PAA having a weight average molecular weight of 800,000 was dissolved in NMP to prepare a 10% by mass PAA/NMP solution, and 6 ml (9.5 mmol in terms of monomer for PAA) of the PAA/NMP solution was taken out and placed in a flask under a nitrogen atmosphere. Separately from the solution, 0.1 g (0.5 mmol) of 4,4'-diaminodiphenylmethane was dissolved in 0.4 ml of NMP to prepare an amine/NMP solution. The whole amount of the amine/NMP solution was dropped into the PAA/NMP solution while stirring the PAA/NMP solution in the flask, and stirring was continued at room temperature for 30 minutes. Thereafter, heating treatment (preheating treatment) was conducted at 130° C. for 3 hours with a Dean-Stark apparatus to obtain an intermediate composition of Comparison Example 1 in a state of an NMP solution.

Next, electrode sheets using as a binder for a negative electrode a polymer compound obtained from each intermediate composition were produced using the obtained intermediate composition of each of Examples 1 and 2. Lithium ion rechargeable batteries were produced using the obtained electrode sheets, and the battery properties of the lithium ion rechargeable batteries were evaluated.

Production of Electrode Sheets

Slurries were each prepared by mixing 85 parts by mass of SiO, 5 parts by mass of acetylene black, and 10 parts by mass of the NMP solution of the intermediate composition of each of Examples 1 and 2 and adding NMP to the resultant mixture. Each slurry was applied to the surface of 30 µm electrolytic copper foil (collector) in a film form using a doctor blade method. NMP in the slurry was volatilized and removed to form a negative electrode active material layer on the electrolytic copper foil. Subsequently, the electrolytic copper foil and the negative electrode active material layer were adhered firmly and joined by compressing the electrolytic copper foil and the negative electrode active material layer such that the thickness of the negative electrode active material layer was 20 μm with a roll press machine.

Thereafter, heating treatment was conducted in vacuum (under reduced pressure) at 160° C. for 2 hours to the negative electrode active material layer in a dried state after NMP was removed, so that the intermediate composition contained in the negative electrode active material layer was subjected to condensation reaction and the negative electrode active material layer was heated and cured. Thereby, electrode sheets each containing as a binder for a negative electrode a polymer compound having a crosslinked structure were obtained.

For comparison, electrode sheets using PAA or PAI (polymer compound having amide bond moiety and imide bond moiety in molecular structure) as a binder for a negative electrode were produced in the same manner. Further, an electrode sheet was produced using the intermediate composition of Reference Example 1 in the same manner.

Production of Lithium Ion Rechargeable Battery

A separator was disposed between a negative electrode (electrode for evaluation) obtained by cutting each electrode sheet into a circle having a diameter of 11 mm and a positive electrode obtained by cutting metallic lithium foil having a thickness of 500 μm into a circle having a diameter of 13 mm to obtain an electrode body battery. In a battery case, the electrode body battery was accommodated and a nonaqueous electrolyte was injected, and the battery case was sealed to obtain a lithium ion rechargeable battery. As the separator, a glass filter manufactured by Hoechst Celanese Corporation and Celgard 2400 manufactured by Celgard, LLC. were used. As the nonaqueous electrolyte, a nonaqueous electrolyte obtained by dissolving lithium hexafluorophosphate in a mixed solvent in which ethylene carbonate and diethyl carbonate were mixed in a volume ratio of 1:1 such that the concentration of the lithium hexafluorophosphate was 1 M was used.

Evaluation of Battery Properties

The obtained lithium ion batteries were discharged at a direct current of 0.2 mA until the voltage at the negative electrode relative to the positive electrode reached 0.01 V, and charged at a direct current of 0.2 mA 10 minutes after the discharge was completed until the voltage at the negative electrode relative to the positive electrode reached 1.0 V. The discharge capacity in this cycle was defined as the initial discharge capacity, and the charge capacity in this cycle was defined as the initial charge capacity. The initial efficiency was calculated based on the following expression. The results are shown in Table 1.

Initial efficiency (%)=(Initial charge capacity/initial discharge capacity)×100

The above-described discharge and charge was counted as 1 cycle, and the specified cycles of charge and discharge were conducted to calculate the cyclability based on the following expression. The results are shown in Table 1.

Cyclability (%)=(Charge capacity after specified cycles/initial charge capacity)×100

TABLE 1

| Test Example | 1 | 2 | 3 | 4 | 5 |
|---|---|---|---|---|---|
| Binder for negative electrode | Example 1 | Example 2 | PAI | PAA | Reference Example 1 |
| Initial discharge capacity (mAh/g) | 1637 | 1737 | 1532 | 1289 | 1763 |
| Initial charge capacity (mAh/g) | 1165 | 1238 | 1055 | 964 | 1263 |
| Initial efficiency (%) | 71.2 | 71.3 | 68.9 | 74.8 | 71.6 |
| Cyclability (%) 20 cycles | 98.5 | 96.6 | 90.2 | 29.5 | 95.5 |

As shown in Table 1, the results were obtained in which both the initial efficiency and the cyclability showed a high value in Test Examples 1 and 2 using Examples 1 and 2 respectively as a binder for a negative electrode. In contrast, the results were obtained in which one of the initial efficiency and the cyclability showed a low value in Test Examples 3 and 4 using PAI and PAA respectively as a binder for a negative electrode. From these results, it was ascertained that the polymer compound of the present invention is useful as a binder for a negative electrode of an electrical storage device such as a rechargeable battery.

Test Examples 1 and 2 using Examples 1 and 2 respectively showed a higher cyclability than Test Example 5 using as a binder for a negative electrode Reference Example 1 where the third compound was not condensed as a binder for a negative electrode. From these results, it was ascertained that the cyclability was improved by introducing phosphorous acid or triethoxysilane in the molecular structure of a binder for a negative electrode.

<Test 2>

Next, the battery properties were evaluated in the case where a silicon material made of a layered polysilane was used as a negative electrode active material. In the present test, the polymer compound obtained from the intermediate composition of Example 1 was used as a binder for a negative electrode.

Preparation of Silicon Material

To 20 ml of concentrated hydrochloric acid cooled in an ice bath at 0° C. and containing hydrogen fluoride with a concentration of 1% by mass, 5 g of CaSi2 were added and stirred for 1 hour, thereafter water was added thereto, and the resultant mixture was further stirred for 5 minutes. A yellow powder obtained by filtering the reaction solution was washed with water and ethanol and dried under a reduced pressure to obtain a layered polysilane. The obtained layered polysilane was heated to 500° C. under an argon atmosphere to obtain a silicon material in which hydrogen was eliminated from the polysilane.

Production of Electrode Sheets

A slurry was prepared by mixing 70 parts by mass of the silicon material, 15 parts by mass of natural graphite, 5 parts by mass of acetylene black, and 10 parts by mass of the NMP solution of the intermediate composition of Example 1 and adding NMP to the resultant mixture. The slurry was applied to the surface of 30 μm electrolytic copper foil as a collector in a film form using a doctor blade method. NMP in the slurry was volatilized and removed to form a negative electrode active material layer on the electrolytic copper foil. Subsequently, the electrolytic copper foil and the negative electrode active material layer were adhered firmly and joined by compressing the electrolytic copper foil and the negative electrode active material layer such that the thickness of the negative electrode active material layer was 20 μm with a roll press machine.

Thereafter, heating treatment was conducted in vacuum (under reduced pressure) at 180° C. for 2 hours to the negative electrode active material layer in a dried state after NMP was removed, so that the intermediate composition contained in the negative electrode active material layer was subjected to condensation reaction and the negative electrode active material layer was heated and cured. Thereby, an electrode sheet containing as a binder for a negative electrode a polymer compound having a crosslinked structure was obtained. Similar electrode sheets were produced using PAI and PAA in place of the NMP solution of the Example. Further, an electrode sheet was produced using the intermediate composition of Reference Example 1 in the same manner.

Evaluation of Battery Properties

Lithium ion rechargeable batteries were produced using the obtained electrode sheets, and the battery properties of the lithium ion rechargeable batteries were evaluated. The results are shown in Table 2. The method of producing a lithium ion rechargeable battery and the method of evaluating the battery properties of a lithium ion rechargeable battery are the same as the above-described method.

TABLE 2

| Test Example | 6 | 7 | 8 | 9 |
|---|---|---|---|---|
| Binder for negative electrode | Example 1 | PAI | PAA | Reference Example 1 |
| Initial discharge capacity (mAh/g) | 1596 | 1650 | 1617 | 1602 |
| Initial charge capacity (mAh/g) | 1266 | 1244 | 1281 | 1274 |
| Initial efficiency (%) | 79.3 | 75.4 | 79.2 | 79.5 |
| Cyclability (%) 30 cycles | 92.5 | 84.3 | 56.1 | 91.1 |

As shown in Table 2, the results were obtained in which both the initial efficiency and the cyclability showed a high value in Test Example 6 using Example 1 as a binder for a negative electrode. In contrast, the results were obtained in which one of or both the initial efficiency and the cyclability showed a low value in Test Examples 7 and 8 using PAI and PAA respectively as a binder for a negative electrode. Test Example 6 using Example 1 showed a higher cyclability than Test Example 9 using as a binder for a negative electrode Reference Example 1 where the third compound was not condensed. From these results, it was ascertained that the polymer compound of the present invention is also useful as a binder for a negative electrode of an electrical storage device such as a rechargeable battery in the case where a silicon material made of a layered polysilane is used as a negative electrode active material.

<Test 3>

Next, the battery properties were evaluated in the case where a polymer compound using a phosphorous acid ester as the third compound was used as a binder for a negative electrode.

Examples 3-1, 3-2, and 3-3: PAA+4,4'-Diaminodiphenylmethane+Triethyl Phosphite

PAA having a weight average molecular weight of 800,000 was dissolved in NMP to prepare a 10% by mass PAA/NMP solution, and 6 ml (9.5 mmol in terms of monomer for PAA) of the PAA/NMP solution was taken out and placed in a flask under a nitrogen atmosphere. Separately from the solution, an amine/NMP solution was prepared in which 0.1 g (0.5 mmol) of 4,4'-diaminodiphenylmethane was dissolved in 0.4 ml of NMP. The whole amount of the amine/NMP solution was dropped into the PAA/NMP solution while stirring the PAA/NMP solution in the flask, and stirring was continued at room temperature for 30 minutes. Thereafter, heating treatment (preheating treatment) was conducted at 130° C. for 3 hours with a Dean-Stark apparatus. To the treated solution, 15 mg (0.09 mmol), 30 mg (0.18 mmol), or 150 mg (0.9 mmol) of triethyl phosphite was added, and the resultant mixture was stirred at room temperature for 6 hours to obtain intermediate compositions (second intermediate compositions) of Examples 3-1, 3-2, and 3-3 in a state of an NMP solution.

As for the intermediate composition of Example 1, intermediate compositions (second intermediate compositions) of Examples 1-1 and 1-2 were obtained in which the amount of compounded phosphorous acid was made different. The amount of compounded phosphorous acid in Examples 1-1 and 1-2 is as shown in Table 3. The intermediate composition of Example 1-1 is the same as the intermediate composition of Example 1. The intermediate composition of Example 1-2 was prepared in the same manner as in Example 1 except that the amount of compounded phosphorous acid was different.

Evaluation of Battery Properties

Electrode sheets using as a binder for a negative electrode a polymer compound obtained from an intermediate composition were produced using the obtained intermediate compositions of Examples 3-1, 3-2, 3-3 and Examples 1-1 and 1-2. Lithium ion rechargeable batteries were produced using the obtained electrode sheets, and the battery properties of the lithium ion rechargeable batteries were evaluated. The results are shown in Table 3. The method of producing an electrode sheet and a lithium ion rechargeable battery and the method of evaluating the battery properties of a lithium ion rechargeable battery are the same as the method of Test 2.

TABLE 3

| Test Example | 10 | 11 | 12 | 13 | 14 |
|---|---|---|---|---|---|
| Binder for negative electrode | Example 3-1 | Example 3-2 | Example 3-3 | Example 1-1 | Example 1-2 |
| Amount of third compound (mmol) | 0.09 | 0.18 | 0.9 | 0.18 | 0.9 |
| Initial discharge capacity (mAh/g) | 1605 | 1585 | 1709 | 1596 | 1677 |
| Initial charge capacity (mAh/g) | 1279 | 1259 | 1376 | 1266 | 1322 |
| Initial efficiency (%) | 79.7 | 79.4 | 80.5 | 79.3 | 78.8 |
| Cyclability (%) 30 cycles | 92.3 | 92.9 | 94 | 92.5 | 86 |

As shown in Table 3, it was ascertained that the initial efficiency and cyclability in Test Example 11 using the polymer compound of Example 3-2 as a binder for a negative electrode were about the same as the initial efficiency and cyclability in Test Example 13 using the same amount of the polymer compound of Example 1-1. From these results, it was ascertained that the polymer compound using a phosphorous acid ester is also useful as a binder for a negative electrode of an electrical storage device such as a rechargeable battery.

From the results of Test Examples 10 to 12, it was ascertained that polymer compound using a phosphorous acid ester tended to increase the cyclability as the amount of the compounded phosphorous acid ester was increased. Particularly, as shown in the results of Text Example 12, the cyclability was also increased in the case where the amount of the compounded phosphite acid ester was increased up to 0.9 mmol. In contrast, from the results of Test Example 14, the cyclability was lowered when the amount of compounded phosphorous acid was increased up to 0.9 mmol in the polymer compound using phosphorous acid. From these results, it is considered that a larger number of phosphoric acid structures can be introduced with a phosphorous acid ester than with phosphorous acid and the larger number of phosphoric acid structures have been introduced, so that the cyclability in Test Example 12 is improved.

<Test 4>

Next, battery properties were evaluated in the case where a polymer compound using phosphoric acid as the third compound was used as a binder for a negative electrode.

Example 4: PAA+4,4'-Diaminodiphenylmethane+ Phosphoric Acid

PAA having a weight average molecular weight of 800,000 was dissolved in NMP to prepare a 10% by mass PAA/NMP solution, and 7 ml (9.5 mmol in terms of monomer for PAA) of the PAA/NMP solution was taken out and placed in a flask under a nitrogen atmosphere. To the solution, 15 μl (0.15 mmol) of phosphoric acid was added, and the resultant mixture was stirred at room temperature for 6 hours. Separately from the solution, 0.1 g (0.5 mmol) of 4,4'-diaminodiphenylmethane was dissolved in 0.4 ml of NMP to prepare an amine/NMP solution. The whole amount of the amine/NMP solution was dropped into the PAA/NMP solution while stirring the PAA/NMP solution in the flask, and stirring was continued at room temperature for 30 minutes. Thereafter, heating treatment (preheating treatment) was conducted at 130° C. for 3 hours with a Dean-Stark apparatus to obtain an intermediate composition of Example 4 in a state of an NMP solution.

Evaluation of Battery Properties

An electrode sheet using as a binder for a negative electrode a polymer compound obtained from an intermediate composition was produced using the obtained intermediate composition of Example 4. A lithium ion rechargeable battery was produced using the electrode sheet. The results are shown in Table 4. The method of producing an electrode sheet and a lithium ion rechargeable battery and the method of evaluating the battery properties of a lithium ion rechargeable battery are the same as the method of Test 1.

TABLE 4

| Test Example | 15 | 3 | 4 | 5 |
|---|---|---|---|---|
| Binder for negative electrode | Example 4 | PAI | PAA | Reference Example 1 |
| Initial discharge capacity (mAh/g) | 1544 | 1532 | 1289 | 1763 |
| Initial charge capacity (mAh/g) | 1073 | 1055 | 964 | 1263 |
| Initial efficiency (%) | 69.5 | 68.9 | 74.8 | 71.6 |
| Cyclability (%) 20 cycles | 98.8 | 90.2 | 29.5 | 95.5 |

As shown in Table 4, the results were obtained in which both the initial efficiency and the cyclability showed a high value in Test Example 15 using Example 4 as a binder for a negative electrode. In contrast, the results were obtained in which one of the initial efficiency and the cyclability showed a low value in Test Examples 3 and 4 using PAI and PAA respectively. From these results, it was ascertained that the polymer compound of the present invention is useful as a binder for a negative electrode of an electrical storage device such as a rechargeable battery.

Test Example 15 using Example 4 showed a higher cyclability than Test Example 5 using as a binder for a negative electrode Reference Example 1 where the third compound was not condensed. From these results, it was ascertained that the cyclability was improved by introducing phosphoric acid in the molecular structure of a binder for a negative electrode.

<Test 5>

Next, changes in the battery properties caused when the molecular weight of a carboxy group-containing vinyl polymer was made different were evaluated in the case where a polymer compound using phosphorous acid as the third compound was used as a binder for a negative electrode.

Example 5: PAA+4,4'-Diaminodiphenylmethane+ Phosphorous Acid

PAA having a weight average molecular weight of 100,000 was dissolved in NMP to prepare a 10% by mass PAA/NMP solution, and 7 ml (9.5 mmol in terms of monomer for PAA) of the PAA/NMP solution was taken out and placed in a flask under a nitrogen atmosphere. Separately from the solution, 0.1 g (0.5 mmol) of 4,4'-diaminodiphenylmethane was dissolved in 0.4 ml of NMP to prepare an amine/NMP solution. The whole amount of the amine/NMP solution was dropped into the PAA/NMP solution while stirring the PAA/NMP solution in the flask, and stirring was continued at room temperature for 30 minutes. Thereafter, heating treatment (preheating treatment) was conducted at 110° C. for 3 hours with a Dean-Stark apparatus. To the treated solution, 15 mg (0.18 mmol) of phosphorous acid was added, and the resultant mixture was stirred at room temperature for 12 hours to obtain an intermediate composition (second intermediate composition) of Example 5 in a state of an NMP solution.

As Reference Example, changes in the battery properties caused when the molecular weight of PAI was made different were also evaluated in the case where PAI was used as a binder for a negative electrode.

Reference Example 2: PAI

In 17.5 g of NMP, 2.503 g (10 mmol) of 4,4'-diaminodiphenylmethane was dissolved to prepare the first NMP solution. Separately from the solution, 1.92 g (10 mmol) of trimellitic anhydride chloride was dissolved in 13.4 g of NMP to prepare the second NMP solution. The second NMP solution was added to the first NMP solution under an inert gas atmosphere, and heating treatment was conducted at 90° C. for 5 hours to obtain an NMP solution (solid content ratio of 12.5% by mass) of PAI having a molecular weight of 20,000.

Reference Example 3: PAI

In 11.4 g of NMP, 2.503 g (10 mmol) of 4,4'-diaminodiphenylmethane was dissolved to prepare the first NMP solution. Separately from the solution, 1.92 g (10 mmol) of trimellitic anhydride chloride was dissolved in 8.75 g of NMP to prepare the second NMP solution. The second NMP solution was added to the first NMP solution under an inert gas atmosphere, and heating treatment was conducted at 80° C. for 3 hours to obtain an NMP solution (solid content ratio of 18% by mass) of PAI having a molecular weight of 5,000.

Evaluation of Battery Properties

Electrode sheets were produced using the intermediate composition of Example 5 and NMP solutions of PAI of Reference Examples 2 and 3. Also, lithium ion rechargeable batteries were produced using the obtained electrode sheets, and the battery properties of the lithium ion rechargeable batteries were evaluated. The results are shown in Table 5. The method of producing a lithium ion rechargeable battery and the method of evaluating the battery properties of a lithium ion rechargeable battery are the same as the method of Test 2.

TABLE 5

| Test Example | 6 | 16 | 17 | 18 |
|---|---|---|---|---|
| Binder for negative electrode | Example 1 | Example 5 | Reference Example 2 | Reference Example 3 |
| Molecular weight of PAA (PAI) | 800,000 | 100,000 | 20,000 | 5,000 |
| Initial discharge capacity (mAh/g) | 1596 | 1603 | 1502 | 1486 |
| Initial charge capacity (mAh/g) | 1266 | 1277 | 1095 | 1091 |
| Initial efficiency (%) | 79.3 | 79.7 | 72.9 | 73.4 |
| Cyclability (%) 30 cycles | 92.5 | 92.6 | 81.1 | 72.5 |

As shown in Table 5, no significant difference in the battery properties was observed for Test Examples 6, 16, and 17 using Examples even in the case where the molecular weight of a carboxy group-containing vinyl polymer (PAA) was made different. In contrast, the cyclability was lowered in Test Examples 17 and 18 using Reference Examples as the molecular weight of PAI was lowered. From these results, it is suggested that lowering of the resin strength caused by lowering of the molecular weight be harder to occur in the polymer compounds obtained from the intermediate composition of Examples than in PAI.

<Test 6>

Next, changes in the battery properties were evaluated for the intermediate composition of Example 1 in the case where the carboxy groups/amino groups ratio was made different by making the compounding ratio of the carboxy group-containing vinyl polymer and the aromatic multifunctional amine different.

Examples 1-1 to 1-3: PAA+4,4'-Diaminodiphenylmethane+Phosphorous Acid

Intermediate compositions of Examples 1-1 to 1-3 each having a different carboxy groups/amino groups ratio were obtained by making the compounding ratio of 4,4'-diaminodiphenylmethane in the intermediate composition of Example 1 different. The carboxy groups/amino groups ratio for each Example is as shown in Table 6. The intermediate composition of Example 1-1 is the same as the intermediate composition of Example 1, and the carboxy groups/amino groups ratio was 9.5. The intermediate compositions of Examples 1-2 to 1-3 were prepared in the same manner as in Example 1 except that the compounding ratio of 4,4'-diaminodiphenylmethane was different.

Evaluation of Battery Properties

Electrode sheets using as a binder for a negative electrode a polymer compound obtained from an intermediate composition were produced using the obtained intermediate compositions of Examples 1-1 to 1-3. Lithium ion rechargeable batteries were produced using the obtained electrode sheets, and the battery properties of the lithium ion rechargeable batteries were evaluated. The results are shown in Table 6. The method of producing an electrode sheet and a lithium ion rechargeable battery and the method of evaluating the battery properties of a lithium ion rechargeable battery were the same as the method of Test 2.

TABLE 6

| Test Example | 6 | 19 | 20 |
|---|---|---|---|
| Binder for negative electrode | Example 1-1 | Example 1-2 | Example 1-3 |
| Carboxy groups/amino groups ratio | 9.5 | 4.75 | 2.0 |
| Initial discharge capacity (mAh/g) | 1596 | 1600 | 1575 |
| Initial charge capacity (mAh/g) | 1266 | 1278 | 1248 |
| Initial efficiency (%) | 79.3 | 79.9 | 79.2 |
| Cyclability (%) 30 cycles | 92.5 | 93.1 | 92.6 |

As shown in Table 6, no significant difference in the battery properties was observed even in the case where the ratio of the carboxy groups to the amino groups was made different.

<Test 7>

Next, changes in the battery properties caused when an aromatic multifunctional amine was made different were evaluated in the case where a polymer compound using phosphorous acid as the third compound was used as a binder for a negative electrode.

Example 6: PAA+3,4'-Diaminodiphenylmethane+Phosphorous Acid

PAA having a weight average molecular weight of 800,000 was dissolved in NMP to prepare a 10% by mass PAA/NMP solution, and 6 ml (9.5 mmol in terms of monomer for PAA) of the PAA/NMP solution was taken out and placed in a flask under a nitrogen atmosphere. Separately from the solution, 0.1 g (0.5 mmol) of 3,4'-diaminodiphenylmethane was dissolved in 0.4 ml of NMP to prepare an amine/NMP solution. The whole amount of the amine/NMP solution was dropped into the PAA/NMP solution while stirring the PAA/NMP solution in the flask, and stirring was continued at room temperature for 30 minutes. Thereafter, heating treatment (preheating treatment) was conducted at 130° C. for 3 hours with a Dean-Stark apparatus. To the treated solution, 15 mg (0.18 mmol) of phosphorous acid was added, and the resultant mixture was stirred at room temperature for 6 hours to obtain an intermediate composition (second intermediate composition) of Example 1 in a state of an NMP solution.

Example 7: PAA+3,3'-Diaminodiphenylmethane+Phosphorous Acid

PAA having a weight average molecular weight of 800,000 was dissolved in NMP to prepare a 10% by mass PAA/NMP solution, and 6 ml (9.5 mmol in terms of monomer for PAA) of the PAA/NMP solution was taken out and placed in a flask under a nitrogen atmosphere. Separately from the solution, an amine/NMP solution was prepared in which 0.1 g (0.5 mmol) of 3,3'-diaminodiphenylmethane was dissolved in 0.4 ml of NMP. The whole amount of the amine/NMP solution was dropped into the PAA/NMP solution while stirring the PAA/NMP solution in the flask, and stirring was continued at room temperature for 30 minutes. Thereafter, heating treatment (preheating treatment) was conducted at 130° C. for 30 minutes with a Dean-Stark apparatus. To the treated solution, 15 mg (0.18 mmol) of phosphorous acid was added, and the resultant mixture was stirred at room temperature for 6 hours to prepare an intermediate composition (second intermediate composition) of Example 1 in a state of an NMP solution.

Example 8: PAA+4,4'-Diaminodiphenylether+Phosphorous Acid

PAA having a weight average molecular weight of 800,000 was dissolved in NMP to prepare a 10% by mass PAA/NMP solution, and 6 ml (9.5 mmol in terms of monomer for PAA) of the PAA/NMP solution was taken out and placed in a flask under a nitrogen atmosphere. Separately from the solution, an amine/NMP solution was prepared in which 100 mg (0.5 mmol) of 4,4'-diaminodiphenylether was dissolved in 1 ml of NMP. The whole amount of the amine/NMP solution was dropped into the PAA/NMP solution while stirring the PAA/NMP solution in the flask, and stirring was continued at room temperature for 30 minutes. Thereafter, heating treatment (preheating treatment) was conducted at 130° C. for 3 hours with a Dean-Stark apparatus. To the treated solution, 15 mg (0.18 mmol) of phosphorous acid was added, and the resultant mixture was stirred at room temperature for 6 hours to prepare an intermediate composition (second intermediate composition) of Example 1 in a state of an NMP solution.

Example 9: PAA+4,4'-Diaminobenzophenone+Phosphorous Acid

PAA having a weight average molecular weight of 800,000 was dissolved in NMP to prepare a 10% by mass PAA/NMP solution, and 6 ml (9.5 mmol in terms of monomer for PAA) of the PAA/NMP solution was taken out and placed in a flask under a nitrogen atmosphere. Separately from the solution, an amine/NMP solution was prepared in which 106 mg (0.5 mmol) of 4,4'-diaminobenzophenone was dissolved in 1 ml of NMP. The whole amount of the amine/NMP solution was dropped into the PAA/NMP solution while stirring the PAA/NMP solution in the flask, and stirring was continued at room temperature for 30 minutes. Thereafter, heating treatment (preheating treatment) was conducted at 130° C. for 3 hours with a Dean-Stark apparatus. To the treated solution, 15 mg (0.18 mmol) of phosphorous acid was added, and the resultant mixture was stirred at room temperature for 6 hours to prepare an intermediate composition (second intermediate composition) of Example 1 in a state of an NMP solution.

Example 10: PAA+Pararosaniline+Phosphorous Acid

PAA having a weight average molecular weight of 800,000 was dissolved in NMP to prepare a 10% by mass PAA/NMP solution, and 6 ml (9.5 mmol in terms of monomer for PAA) of the PAA/NMP solution was taken out and placed in a flask under a nitrogen atmosphere. Separately from the solution, an amine/NMP solution was prepared in which 153 mg (0.5 mmol) of pararosaniline was dissolved in 2 ml of NMP. The whole amount of the amine/NMP solution was dropped into the PAA/NMP solution while stirring the PAA/NMP solution in the flask, and stirring was continued at room temperature for 30 minutes. Thereafter, heating treatment (preheating treatment) was conducted at 130° C. for 3 hours with a Dean-Stark apparatus. To the treated solution, 15 mg (0.18 mmol) of phosphorous acid was added, and the resultant mixture was stirred at room temperature for 6 hours to prepare an intermediate composition (second intermediate composition) of Example 1 in a state of an NMP solution.

Example 11: PAA+4,4'-Methylenebis(2-Ethyl-6-Methylaniline)+Phosphorous Acid

PAA having a weight average molecular weight of 800,000 was dissolved in NMP to prepare a 10% by mass PAA/NMP solution, and 6 ml (9.5 mmol in terms of monomer for PAA) of the PAA/NMP solution was taken out and placed in a flask under a nitrogen atmosphere. Separately from the solution, an amine/NMP solution was prepared in which 141 mg (0.5 mmol) of 4,4'-methylenebis(2-ethyl-6-methylaniline) was dissolved in 2 ml of NMP. The whole amount of the amine/NMP solution was dropped into the PAA/NMP solution while stirring the PAA/NMP solution in the flask, and stirring was continued at room temperature for 30 minutes. Thereafter, heating treatment (preheating treatment) was conducted at 130° C. for 3 hours with a Dean-Stark apparatus. To the treated solution, 15 mg (0.18 mmol) of phosphorous acid was added, and the resultant mixture was stirred at room temperature for 6 hours to prepare an intermediate composition (second intermediate composition) of Example 1 in a state of an NMP solution.

Example 12: PAA+2,2'-Bis(4-Aminophenyl)Hexafluoropropane+Phosphorous Acid

PAA having a weight average molecular weight of 800,000 was dissolved in NMP to prepare a 10% by mass PAA/NMP solution, and 6 ml (9.5 mmol in terms of monomer for PAA) of the PAA/NMP solution was taken out and placed in a flask under a nitrogen atmosphere. Separately from the solution, an amine/NMP solution was prepared in which 167 mg (0.5 mmol) of 2,2'-bis(4-aminophenyl) hexafluoropropane was dissolved in 2 ml of NMP. The whole amount of the amine/NMP solution was dropped into the PAA/NMP solution while stirring the PAA/NMP solution in the flask, and stirring was continued at room temperature for 30 minutes. Thereafter, heating treatment (preheating treatment) was conducted at 130° C. for 3 hours with a Dean-Stark apparatus. To the treated solution, 15 mg (0.18 mmol) of phosphorous acid was added, and the resultant mixture was stirred at room temperature for 6 hours to prepare an intermediate composition (second intermediate composition) of Example 1 in a state of an NMP solution.

Evaluation of Battery Properties

Electrode sheets using as a binder for a negative electrode a polymer compound obtained from an intermediate composition were produced using the obtained intermediate compositions of Examples 6 to 12. Lithium ion rechargeable batteries were produced using the obtained electrode sheets, and the battery properties of the lithium ion rechargeable batteries were evaluated. The results are shown in Table 7 and Table 8. The method of producing an electrode sheet and a lithium ion rechargeable battery and the method of evaluating the battery properties of a lithium ion rechargeable battery are the same as the method of Test 2.

TABLE 7

| Test Example | 6 | 21 | 22 | 23 |
|---|---|---|---|---|
| Binder for negative electrode | Example 1 | Example 6 | Example 7 | Example 8 |
| Initial discharge capacity (mAh/g) | 1596 | 1599 | 1591 | 1601 |
| Initial charge capacity (mAh/g) | 1266 | 1264 | 1263 | 1271 |
| Initial efficiency (%) | 79.3 | 79.1 | 79.4 | 79.4 |
| Cyclability (%) 30 cycles | 92.5 | 92.0 | 92.2 | 93.0 |

TABLE 8

| Test Example | 6 | 24 | 25 | 26 |
|---|---|---|---|---|
| Binder for negative electrode | Example 9 | Example 10 | Example 11 | Example 12 |
| Initial discharge capacity (mAh/g) | 1544 | 1512 | 1495 | 1501 |
| Initial charge capacity (mAh/g) | 1222 | 1201 | 1171 | 1182 |
| Initial efficiency (%) | 79.2 | 79.4 | 78.3 | 78.75 |
| Cyclability (%) 30 cycles | 91.1 | 93.2 | 90.9 | 91.6 |

As shown in Table 7 and Table 8, no significant difference in the battery properties was observed even in the case where the aromatic multifunctional amine was made different.

The invention claimed is:

1. A negative electrode of an electrical storage device, comprising:
   a binder for a negative electrode, including a polymer compound obtained by condensing:
   a carboxy group-containing vinyl polymer;
   an aromatic multifunctional amine; and
   a third compound selected from phosphorous acid, phosphorous acid ester, trialkoxysilane, and phosphoric acid,
   wherein the aromatic multifunctional amine is a multifunctional amine represented by the following formula (1),

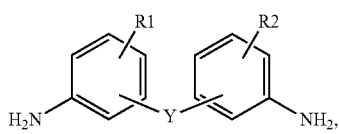

(1)

wherein Y represents a straight chain alkyl group having 1 to 4 carbon atoms, a phenylene group, or an oxygen atom, R1 and R2 each independently represent one or more hydrogen atoms, methyl groups, ethyl groups, trifluoromethyl groups, or methoxy groups; and
   a negative electrode active material,
   wherein the negative electrode active material is at least one selected from carbon-based materials capable of intercalating and deintercalating lithium, elements capable of producing alloy with lithium, and compounds including an element capable of producing alloy with lithium.

2. The negative electrode according to claim 1, wherein the negative electrode active material is at least one selected from: silicon materials obtained from $CaSi_2$ through decalcification reaction; Si; and $SiO_v$ ($0<v<2$).

3. An electrical storage device comprising:
   the negative electrode according to claim 1; and
   a nonaqueous electrolyte.

4. The negative electrode of an electrical storage device according to claim 1, wherein the polymer compound comprises
   a chain structure constituted by the carboxy group-containing vinyl polymer; and
   a crosslinked structure connecting carboxylic acid side chains in the chain structure or between, the chain structures, wherein the crosslinked structure is at least one crosslinked structure selected from the following formulas (3) to (5), and at least one selected from a phosphoric acid group, a phosphate group, and a trialkoxysilane group is added to a carboxy group contained in the chain structure

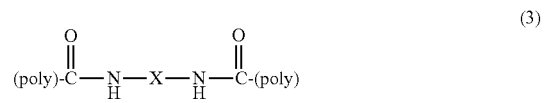

(3)

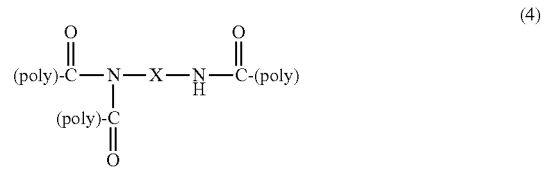

(4)

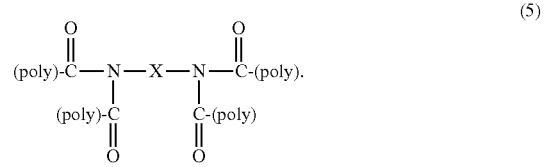

(5)

5. A negative electrode of an electrical storage device, comprising:
   a binder for a negative electrode, including a polymer compound obtained by condensing a carboxy group-containing vinyl polymer and an aromatic multifunctional amine,
   wherein at least one selected from a phosphoric acid group, a phosphoric acid ester group, and a trialkoxysilane groups is added to a carboxy group in the polymer compound, and
   wherein the aromatic multifunctional amine is a multifunctional amine represented by the following formula (1),

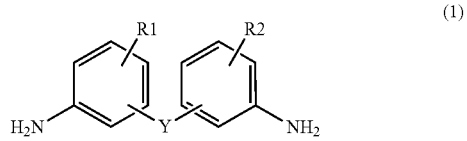

(1)

wherein Y represents a straight chain alkyl group having 1 to 4 carbon atoms, a phenylene group, or an oxygen atom, R1 and R2 each independently represent one or more hydrogen atoms, methyl groups, ethyl groups, trifluoromethyl groups, or methoxy groups; and
   a negative electrode active material,
   wherein the negative electrode active material is at least one selected from carbon-based materials capable of intercalating and deintercalating lithium, elements capable of producing alloy with lithium, and compounds including an element capable of producing alloy with lithium.

6. The negative electrode according to claim 5, wherein the negative electrode active material is at least one selected from: silicon materials obtained from $CaSi_2$ through decalcification reaction; Si; and $SiO_v$, ($0<v<2$).

7. An electrical storage device comprising:
the negative electrode according to claim 5, and
a nonaqueous electrolyte.

8. The negative electrode of an electrical storage device according to claim 5, wherein the polymer compound comprises:
a chain structure constituted by the carboxy group-containing vinyl polymer; and
a crosslinked structure connecting carboxylic acid side chains in the chain structure or between the chain structures, wherein the crosslinked structure is at least one crosslinked structure selected from the following formulas (3) to (5), and at least one selected from a phosphoric acid group, a phosphate group, and a tri-alkoxysilane group is added to a carboxy group contained in the chain structure

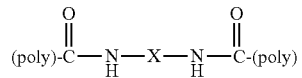

(3)

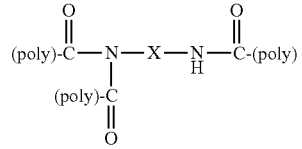

(4)

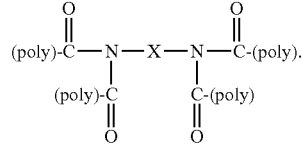

(5)

* * * * *

UNITED STATES PATENT AND TRADEMARK OFFICE
CERTIFICATE OF CORRECTION

PATENT NO. : 10,707,490 B2  
APPLICATION NO. : 15/528776  
DATED : July 7, 2020  
INVENTOR(S) : Yusuke Sugiyama et al.

Page 1 of 1

It is certified that error appears in the above-identified patent and that said Letters Patent is hereby corrected as shown below:

On the Title Page

Item (73), Assignee; delete "Toyota-shi, Aichi-ken (JP)" and insert -- Kariya-shi, Aichi-ken (JP) --

Signed and Sealed this  
Thirteenth Day of October, 2020

Andrei Iancu  
*Director of the United States Patent and Trademark Office*